United States Patent [19]

Leupold et al.

[11] Patent Number: 5,210,259
[45] Date of Patent: May 11, 1993

[54] PROCESS FOR THE OXIDATION OF DIALKYL ESTERS OF 2-HYDROXY-ETHYLPHOSPHONIC ACID

[75] Inventors: Ernst I. Leupold, Neu-Anspach; Günter Roscher, Kelkheim/Taunus, both of Fed. Rep. of Germany

[73] Assignee: Hoechst Aktiengesellschaft, Frankfurt am Main, Fed. Rep. of Germany

[21] Appl. No.: 859,416
[22] PCT Filed: Nov. 20, 1990
[86] PCT No.: PCT/EP90/01980
§ 371 Date: May 22, 1992
§ 102(e) Date: May 22, 1992
[87] PCT Pub. No.: WO91/08210
PCT Pub. Date: Jun. 13, 1991

[30] Foreign Application Priority Data

Nov. 27, 1989 [DE] Fed. Rep. of Germany ....... 3939142

[51] Int. Cl.$^5$ .................. C07F 9/40; C07F 9/6571
[52] U.S. Cl. ............................. 558/86; 558/87; 558/129; 558/130; 558/85
[58] Field of Search ............. 558/86, 87, 129, 130, 558/85

[56] References Cited

U.S. PATENT DOCUMENTS 4,151,172  4/1979  Ondetti et al. ............... 260/326.2

FOREIGN PATENT DOCUMENTS 1353779  11/1987  U.S.S.R. ..................... 558/87

*Primary Examiner*—Marianne M. Cintins
*Assistant Examiner*—Margaret J. Page

[57] ABSTRACT

A process for the preparation of diesters of carboxymethylphosphonic acid of the formula: $(RO)_2P(O)CH_2CO_2H$, in which R is a straight-chain or branched alkyl radical having 1 to 20 carbon atoms, a cycloaliphatic radical having 5 to 8 carbon atoms, a phenyl or naphthyl radical which can be substituted, an aralkyl radical having 7 to 10 carbon atoms, or in which the $(RO)_2P$ group forms a ring having 2 to 5 carbon atoms which can be substituted, characterized in that dialkyl ester of 2-hydroxyethylphosphonic acid of the formula $(RO)_2P(O)CH_2CH_2OH$, in which R has the abovementioned meaning, is reacted with oxygen in the presence of water and a catalyst which contains at least one metal selected from the platinum metals group.

15 Claims, No Drawings

PROCESS FOR THE OXIDATION OF DIALKYL ESTERS OF 2-HYDROXY-ETHYLPHOSPHONIC ACID

The present invention relates to a process for the preparation of dialkyl esters of carboxymethylphosphonic acid by oxidation of the corresponding dialkyl esters of 2-hydroxyethylphosphonic acid with oxygen in the presence of a catalyst.

Dialkyl esters of carboxymethylphosphonic acid can be used as complexing agents or as intermediates in the preparation of organophosphorus products.

It is known to prepare diethyl esters of carboxymethylphosphonic acid by heating benzyl chloroacetate with triethylphosphite and subsequent hydrogenolysis of the benzyl ester of the diethyl esters of carboxymethylphosphonic acid obtained as an intermediate. Di-n-butyl carboxymethylphosphonate had been prepared in an analogous fashion. (D. J. Martin, C. E. Griffin, J. Org. Chem. 30 [1965] 4034). Diethyl ester of carboxymethylphosphonic acid has also been prepared from the corresponding ethyl ester by partial hydrolysis with an equimolar amount of KOH in aqueous ethanol. The corresponding dimethyl ester was prepared from the methyl ester of dimethyl carboxymethylphosphonates by partial hydrolysis with KOH in methanol, and the corresponding di-n-butyl ester from the tributyl ester by partial hydrolysis with aqueous KOH (R. A. Malevannaya et al., Zh. Obshch. Khim. 41 [1971] 1426–1434).

However, in the hydrolysis of triesters of carboxymethylphosphonic acid in alkaline medium, by-products are frequently produced, since, apart from the ester group, the P-alkoxy group can also be hydrolytically cleaved. With the use of KOH, the subsequent work-up leads, moreover, to the formation of a stoichiometric amount of salt, the removal of which poses problems.

The aim was therefore to develop a process which delivers dialkyl esters of carboxymethylphosphonic acid in high yield and purity, without producing large amounts of unwanted salt at the same time. The present invention now makes such a process available.

The object of the present invention is a process for the preparation of dialkyl esters of carboxymethylphosphonic acid of the formula $(RO)_2P(O)CH_2CO_2H$, in which R is a straight-chain or branched alkyl radical having 1 to 20 carbon atoms, preferably having 1 to 8 carbon atoms, a cycloaliphatic radical having 5 to 8 carbon atoms, a phenyl or naphthyl radical which can be substituted, an aralkyl radical having 7 to 10 carbon atoms, or in which the $(RO)_2P$ group forms a ring which contains 2 to 5 carbon atoms which can be substituted, characterized in that dialkyl ester of 2-hydroxyethylphosphonic acid of the formula $(RO)_2P(O)CH_2CH_2OH$, in which R has the above-mentioned meaning, is reacted with oxygen in the presence of water and a catalyst which contains at least one metal selected from the platinum metals group.

The substituents on the phenyl or naphthyl radical are preferably one or more alkyl radicals having 1 to 6 carbon atoms, alkoxy having 1 to 6 carbon atoms or halogen, preferably chlorine or bromine. As an alkyl radical or cycloaliphatic radical, R can also contain heteroatoms, preferably oxygen or nitrogen.

Metals selected from the platinum metals group which may be mentioned are for example platinum, palladium, iridium, rhodium and ruthenium, palladium and/or platinum being preferred. Particular preference is given to catalysts which exclusively contain platinum as the metal of the platinum group.

The metals mentioned are preferably applied to a support, in particular activated charcoal. The weight fraction of the metals in this case is expediently 1 to 10% of the total weight of the catalyst. Suitable catalysts are for example commercial catalysts having 5 to 10% by weight of platinum on activated charcoal.

In the process according to the invention, it is expedient to add to the starting material a quantity of water such that the content of dialkyl ester of hydroxyethylphosphonic acid in the resulting solution is 5 to 30% by weight, preferably 10 to 20% by weight.

The preferred oxidant is pure oxygen. However, mixtures of oxygen with gases inert to the reactants under the reaction conditions can alternatively be used, for example in the form of air, for example mixtures of oxygen with inert gases or with air.

The total pressure is generally between 0.5 and 100 bar. The reaction velocity increases markedly with increasing parial [sic] pressure of oxygen. However, the advantages offered by the increased reaction velocity at elevated $O_2$ partial pressure can be at least made up for by the resulting substantially greater expenditure in terms of apparatus. A total pressure of 1 to 10 bar is expedient, employment of atmospheric pressure being particularly simple.

The process according to the invention is generally carried out at a temperature of 30° C. up to the boiling point of the aqueous medium, preferably of 50° to 95° C., in particular 60° to 90° C.

The process according to the invention proceeds in a three-phase system of solid catalyst, aqueous medium and gaseous oxygen. It can be carried out in all apparatuses which are suitable for carrying out reactions in the liquid phase with or without employment of overpressure. Examples of this are carrying out the reaction in a stirred vessel or in a bubble column with suspended catalyst. However, the oxidation can also be carried out on a fixed bed with a granular catalyst in a trickle phase reactor.

The reaction time required for the formation of the particular desired reaction product is expediently determined by removing samples of the liquid reaction mixture at certain periods of time and analyzing them. For example, the yield of reaction product can be continuously determined in a simple manner by analysis of a sample with the aid of high pressure liquid chromatography in comparison to standard solutions. It is recommended to optimize the reaction conditions so that the reaction time is as short as possible, since an unnecessarily prolonged introduction of oxygen can lead to hyperoxidations, for example to decarboxylations, and thus to a loss in yield of the desired reaction product.

The starting materials for the process according to the invention are known or can be prepared by process procedures known in principle, cf. for example Chelientsev, Kuskov, Zhur. Obsh. Chei Khim., 16, [1946], 1481.

The reaction mixture can be worked up by conventional methods. In a suitable process, the water is first removed by distillation. A subsequent purification is generally not required; the purities are greater than 90%.

The process according to the invention has the advantage, compared to the conventional processes mentioned in the introduction, that the formation of unwanted products, such as inorganic salts, is avoided. In the catalytic oxidation according to the invention, apart from the desired products, only water is unavoidably formed, which is present in any case in the reaction medium.

EXAMPLES 1. 80 l (S.T.P)/h of oxygen at 80° C. were introduced from below through a glass frit into an externally heated vertically arranged glass tube (diameter 50 mm, length 1200 mm), which had been filled with a mixture of 182 g of diethyl hydroxyethylphosphonate, 728 g of water and 45 g of a commercial catalyst (5% platinum on activated charcoal). After 9 hours, the reaction solution contained 157 g of diethyl carboxymethylphosphonate, corresponding to a yield of 86% of theory.

2. 154 g of dimethyl hydroxyethylphosphonate are reacted for 12 hours at 60° C. analogously to Example 1. The reaction mixture contained 160 g of dimethyl carboxymethylphosphonate, corresponding to a yield of 95% of theory.

We claim:

1. A process for the preparation of diesters of carboxymethylphosphonic acid of the formula $(RO)_2P(O)CH_2CO_2H$, in which R is a straight-chain or branched alkyl radical having 1 to 20 carbon atoms, a cycloaliphatic radical having 5 to 8 carbon atoms, a phenyl or naphthyl radical which can be substituted, an aralkyl radical having 7 to 10 carbon atoms, or in which the $(RO)_2P$ group forms a ring which contains 2 to 5 carbon atoms which can be substituted, which comprises: reacting diesters of 2-hydroxyethylphosphonic acid of the formula $(RO)_2P(O)CH_2CH_2OH$, in which R has the abovementioned meaning, with oxygen in the presence of water and a solid catalyst which contains at least one metal selected from the platinum metals group.

2. The process according to claim 1, wherein R is an alkyl radical having 1 to 8 carbon atoms.

3. The process according to claim 1, wherein the catalyst contains platinum and/or palladium.

4. The process according to claim 1, wherein said metal consists essentially of platinum.

5. The process according to claim 1, wherein the catalyst comprises 1 to 10% by weight of at least one metal selected from the platinum metals group and a support material.

6. The process according to claim 5, wherein said support material comprises activated charcoal.

7. The process according to claim 1, wherein the reaction is carried out in the presence of a quantity of water such that the content of diester of hydroxyethylphosphonic acid in the resulting solution is 5 to 30% by weight.

8. The process according to claim 7, wherein said content of diester of hydroxyethylphosphonic acid in the resulting solution is 10 to 20% by weight.

9. The process according to claim 1, wherein a total pressure of 0.5 to 100 bar is employed.

10. The process according to claim 9, wherein said total pressure is in the range of 1 to 10 bar.

11. The process according to claim 9, wherein said total pressure is atmospheric pressure.

12. The process according to claim 1, wherein the reaction is carried out at a temperature of 30° C. up to the boiling point of the reaction medium.

13. The process according to claim 12, wherein said temperature is in the range of 50° to 95° C.

14. The process according to claim 12, wherein said temperature is in the range of 60° to 90° C.

15. The process according to claim 1, wherein the oxygen is used in a mixture with a gas inert to the reactants under the reaction conditions.

* * * * *